United States Patent
Bartorelli et al.

(10) Patent No.: US 9,492,512 B2
(45) Date of Patent: *Nov. 15, 2016

(54) COMBINATION OF GROWTH FACTORS, CYTOKINES, ANTIBACTERIAL/ANTIVIRAL FACTORS, STEM CELL STIMULATING FACTORS, COMPLEMENT PROTEINS C3A/C4A, AND CHEMOTACTIC FACTORS

(71) Applicant: INNOMED S.A., Luxembourg (LU)

(72) Inventors: Alberto Bartorelli, Crans sur Sierre (CH); Maria Rosa Gobbi, Fino Mornasco (IT)

(73) Assignee: INNOMED S.A., Luxembourg (LU)

( * ) Notice: Subject to any disclaimer, the term of this patent is extended or adjusted under 35 U.S.C. 154(b) by 0 days.

This patent is subject to a terminal disclaimer.

(21) Appl. No.: 14/369,146

(22) PCT Filed: Dec. 27, 2012

(86) PCT No.: PCT/EP2012/076960
§ 371 (c)(1),
(2) Date: Jun. 26, 2014

(87) PCT Pub. No.: WO2013/098331
PCT Pub. Date: Jul. 4, 2013

(65) Prior Publication Data
US 2015/0010497 A1    Jan. 8, 2015

(30) Foreign Application Priority Data

Dec. 30, 2011 (IT) ............................... MI2011A2437
Dec. 30, 2011 (IT) ............................... MI2011A2438
Dec. 30, 2011 (IT) ............................... MI2011A2442
Dec. 30, 2011 (IT) ............................... MI2011A2444

(51) Int. Cl.

| | | |
|---|---|---|
| A61K 38/47 | (2006.01) | |
| A61K 35/16 | (2015.01) | |
| A61K 35/20 | (2006.01) | |
| A61K 35/50 | (2015.01) | |
| A61K 38/18 | (2006.01) | |
| A61K 38/19 | (2006.01) | |
| A61K 38/20 | (2006.01) | |
| A61K 38/21 | (2006.01) | |
| A61K 38/40 | (2006.01) | |
| A61K 38/44 | (2006.01) | |

(52) U.S. Cl.
CPC ............... *A61K 38/47* (2013.01); *A61K 35/16* (2013.01); *A61K 35/20* (2013.01); *A61K 35/50* (2013.01); *A61K 38/18* (2013.01); *A61K 38/185* (2013.01); *A61K 38/1808* (2013.01); *A61K 38/1825* (2013.01); *A61K 38/1833* (2013.01); *A61K 38/1841* (2013.01); *A61K 38/1858* (2013.01); *A61K 38/1866* (2013.01); *A61K 38/1875* (2013.01); *A61K 38/19* (2013.01); *A61K 38/191* (2013.01); *A61K 38/193* (2013.01); *A61K 38/20* (2013.01); *A61K 38/204* (2013.01); *A61K 38/2006* (2013.01); *A61K 38/206* (2013.01); *A61K 38/208* (2013.01); *A61K 38/2013* (2013.01); *A61K 38/2026* (2013.01); *A61K 38/2053* (2013.01); *A61K 38/2066* (2013.01); *A61K 38/2086* (2013.01); *A61K 38/217* (2013.01); *A61K 38/40* (2013.01); *A61K 38/44* (2013.01); *C12Y 111/01007* (2013.01); *C12Y 302/01017* (2013.01)

(58) Field of Classification Search
None
See application file for complete search history.

(56) References Cited

U.S. PATENT DOCUMENTS

2014/0369957 A1    12/2014    Bartorelli et al.

FOREIGN PATENT DOCUMENTS

| EP | 0743060 A1 | 11/1996 |
|---|---|---|
| WO | WO 94/10203 A2 | 5/1994 |
| WO | WO 95/00155 A1 | 1/1995 |
| WO | WO 2006/029518 A1 | 3/2006 |
| WO | WO 2007/128737 A2 | 11/2007 |
| WO | WO 2008/003688 A1 | 1/2008 |

OTHER PUBLICATIONS

Anonymous; "Anti-Aging Laennec Placenta"; http://www.made-in-china.com/traderoom/tgveurostar/offer-detailMbnEfhtruUaZ/Sell-Anti-Aging-Laennec-Placenta.html (Aug. 31, 2011).
Anonymous; "Highly popular placenta injection in cosmetic surgery"; http://btob.ex-medical.com/services/sample_placenta_2-2.pdf (May 19, 2011).
Chandana et al.; "Humanized stem cell culture techniques: the animal serum controversy"; Humanized Stem Cell Culture Techniques: The Animal Serum Controversy; vol. 2011, No. 2011, pp. 1-14 (Jan. 1, 2011).

(Continued)

*Primary Examiner* — Brian J Gangle
*Assistant Examiner* — Andrea McCollum
(74) *Attorney, Agent, or Firm* — Perkins Coie LLP; Viola T. Kung (57) ABSTRACT

The present invention refers to a combination of growth factors, cytokines, antibacterial/antiviral factors, stem cell stimulating factors, complement proteins C3a/C4a, and chemotactic factors. The invention also relates to a process for the preparation of said combination from serum, placenta or colostrum and to composition containing said combination for use in the treatment of conditions requiring tissue repair and regeneration and for the substitution of stem cell therapies.

12 Claims, 1 Drawing Sheet

(56) References Cited

OTHER PUBLICATIONS

Colostrum Product Distributor Ltd.; "Holvita TM liquid colostrum extract"; http://web.archive.org/web/20090203022434/http://holvita.co.uk/product_info/liquid_extract.html (Feb. 3, 2009).
International Search Report and Written Opinion of International Application No. PCT/EP2012/076960 with a mailing date of May 3, 2013.
Jeongrai et al.; "Effect of a growth protein-colostrum fraction* on bone development in juvenile rats"; Bioscience Biotechnology Biochemistry, Japan Society for Bioscience, Biotechnology, and Agrochemistry, Tokyo, Japan; vol. 72, No. 1, pp. 1-6 (Jan. 1, 2008).
Jeongrai et al.; "Effect of colostrum basic protein from colostrum whey protein: increases in osteoblast proliferation and bone metabolism"; Journal of Food Science and Nutrition, Korean Society of Food and Nutrition, Pusan, KR; vol. 12, pp. 1-6 (Jan. 1, 2007).
Nitsch et al.; "The clinical use of bovine colostrum"; Journal of Orthomolecular Medicine, Regina, CA; vol. 13, No. 2, pp. 110-118 (Jun. 1, 1998).
Zimecki et al.; "Milk-derived proteins and peptides of potential therapeutic and nutritive value"; Journal of Experimental Therapeutics and Oncology, Rapid Science Publishers, London, GB; vol. 6, No. 2, pp. 89-106 (Jan. 1, 2007).
Gao, "Skin, connective tissue and bone growth promoting composition"; WPI/Thomson; vol. 2005, No. 25, 1 page (Abstract)(Dec. 29, 2004).
Kim et al.; "Isolated whey protein fraction from colostrum of mammalia and food compostion comprising the fractuion are useful for treating and preventing osteoporosis"; WPI/Thomson; vol. 2006, No. 70, 1 page (Abstract)(Dec. 1, 2005).
Non-Final Office action dated Oct. 7, 2015 for U.S. Appl. No. 14/369,127, pp. 1-12.
Won et al., "The effect of human placenta extract in a wound healing model"; Medline; 1 page (Abstract)(Jul. 1, 2010).
Bennett, G. et al., "A Peripheral Moneuropathy in Rat that Produces Disorders of Pain Sensation like those Seen in Man", (1988) Pain, vol. 33, pp. 87-107.
Caplan, A., et al., "Mesenchymal Stem Cells as Trophic Mediators", Journal of Cellular Biochemistry 98 (2006) pp. 1076-1084.
Garber, S., et al., "The Effect of Hyperglycemia on Pulpal Healing in Rats", JOE (2009), vol. 35, No. 1, pp. 60-64.
Pouliot, Y., et al., "Milk Growth Factors as Health Products: Some Technological Aspects", International Diary Journal, (2006), vol. 16, pp. 1415-1420.
Struff, W.G., et al., "Bovine Colostrum as a Biologic in Clinical Medicine: A Review-Part II", International Journal of Clinical Pharmacology and Therapeutics, (2008),vol. 46, No. 5, pp. 211-225.
Zuk, P., et al., Multilineage Cells from Human Adipose Tissue: Implications for Cell-Based Therapies, Tissue Engineering (2001), vol. 7, No. 2, pp. 211-228.

COMBINATION OF GROWTH FACTORS, CYTOKINES, ANTIBACTERIAL/ANTIVIRAL FACTORS, STEM CELL STIMULATING FACTORS, COMPLEMENT PROTEINS C3A/C4A, AND CHEMOTACTIC FACTORS

This application is a National Stage of International Application PCT/EP2012/076960, filed Dec. 27, 2012, published Jul. 4, 2013, under PCT Article 21(2) in English; which claims the priority of Italian Application Nos. M12011A002437, M12011A002438, M12011A002442, M12011A002444, all filed Dec. 30, 2011. The contents of the above-identified applications are incorporated herein by reference in their entireties.

The present invention refers to a combination of growth factors, cytokines, antibacterial/antiviral factors, stem cell stimulating factors, complement proteins C3a/C4a, and chemotactic factors. The invention also relates to a process for the preparation of said combination from serum, placenta or colostrum and to composition containing said combination for use in the treatment of conditions requiring tissue repair and regeneration and for the substitution of stem cell therapies.

BACKGROUND OF THE INVENTION

According to the current scientific literature, the therapeutic action of stem cells may be due to two mechanisms: differentiation of stem cells into resident cells and release of regenerative trophic factors by stem cells. The respective contributions of these two mechanisms remain to be clarified, although it has been suggested that stem cells do not develop into mature cells of the injured tissue, but they rather convey vital factors to this tissue, which can then return to proliferate and differentiate, regenerating itself) AI Caplan and JE Denni, Mesenchymal Stem Cells as Trophic Mediators. Bioch J. Cell 98:1076-1084, 2006).

Stem cell therapy has many problems related not only to the costs and technical and practical complications but also ethical and religious scruples.

Stem cell therapy is feasible only by injection or, in some cases, topically, and not orally The supernatant of cultured stem cells contains growth factors, cytokines, chemotactic factors etc., which are believed to be responsible for the beneficial effect of stem cell therapy on tissue growth and/or repair.

The use of the vital factors isolable from the supernatant of stem cells has, however, not only the same ethical problems of the use of the stem cells themselves but also very high costs.

It is known that some mammalian tissues and biological fluids, namely serum, placenta and colostrum, contain cytokines, growth factors, chemotactic factors, and other components usually found also in the supernatant of stem cell cultures.

Several therapeutic applications have been disclosed in the past for pure colostrum or of extracts or fractions thereof as well as for placenta extracts. For instance, a review of clinical uses of colostrum is reported in Alternative Medicine Review 8(4), 2003, page 378 and in Int. J. Clin. Pharmacol and Therap., 46(5), 2008, 211-225 and in International Dairy Journal, 16, 2006, 1415-1420.

Therapeutic uses of colostrum or fractions thereof are also reported in EP 743060, WO 98/51316, WO 94/16675, WO 98/36759, WO 95/00155, WO 2007/000648, FR 2487676, WO 98/14473, WO 99/64022, WO 2008/103023 and in WO 2006/029494. The latter discloses the extraction of growth and differentiating factors from colostrum but the process disclosed necessarily involves the loss of important components of pure colostrum. None of the prior art documents discloses compositions derived from easily available mammalian sources containing most of if not all components of stem cell cultures supernatant, as a substitute for stem cell therapy.

DESCRIPTION OF THE INVENTION

It has been found that a combination of growth factors, cytokines, antibacterial/antiviral factors, stem cell stimulating factors, complement proteins C3a/C4a, and chemotactic factors is particularly effective in the treatment of a number of pathologies thanks to their multifunctional activities on different biological targets.

The combination of the invention is characterized by a content of:

Cytokines: from about 50 to about 500 pg/mg, preferably from 71.46 to 340.76;

Growth factors: from about 1000 to about 7000 pg/mg, preferably from 1321.80 to 6494.40;

Chemotactic factors: from about 5 to 50 pg/mg, preferably from 6 to 24;

Stem cell stimulating factors: from about 100 to 1500 pg/mg, preferably from 191 to 1105;

Antibacterial/antiviral factors: from about 15 to 80 µg/mg, preferably from 18 to 75;

Complement C3a/C4a proteins: from about 1 to 5 pg/mg, preferably from 1.10 to 2.70.

The cytokines present in the combination of the invention, hereinafter referred to as PMF, are reported in Table 1:

TABLE 1

| Cytokines in PMF (pg/mg) | | |
|---|---|---|
| | Val min | Val max |
| IL-1a | 0.80 | 2.90 |
| IL-1b | 0.02 | 0.09 |
| IL-2 | 1.00 | 10.00 |
| IL-4 | 0.04 | 0.17 |
| IL-6 | 1.00 | 5.00 |
| IL-8 | 0.10 | 0.70 |
| IL-9 | 0.50 | 7.00 |
| IL-10 | 0.50 | 2.80 |
| IL-12 | 1.50 | 2.10 |
| IL-15 | 1.00 | 10.00 |
| IL-17 | 20.00 | 150.00 |
| INF gamma | 5.00 | 50.00 |
| TNFα | 30.00 | 70.00 |
| IL-1 Ra | 10.00 | 30.00 |
| Total | 71.46 | 340.76 |

The growth factors present in the combination of the invention are reported in Table 2:

TABLE 2

| Growth factors in PMF (pg/mg) | | |
|---|---|---|
| | Val min | Val max |
| TGF-β1 | 100.00 | 500.00 |
| IGF-1 | 1000.00 | 5000.00 |
| NGF | 2.00 | 5.00 |

TABLE 2-continued

Growth factors in PMF (pg/mg)

|  | Val min | Val max |
|---|---|---|
| PDGF | 10.00 | 50.00 |
| EGF | 4.80 | 9.40 |
| BMP2 | 15.00 | 50.00 |
| b.FGF | 100.00 | 500.00 |
| FGF-2 | 5.00 | 20.00 |
| HGF | 50.00 | 100.00 |
| VEGF | 35.00 | 260.00 |
| Total | 1321.80 | 6494.40 |

The stem cell stimulating factors present in the combination of the invention are reported in Table 3:

TABLE 3

Stem cell stimulating factors in PMF (pg/mg)

|  | Val min | Val max |
|---|---|---|
| G-CSF | 10.00 | 50.00 |
| GM-CSF | 100.00 | 750.00 |
| LIF | 50.00 | 200.00 |
| SCF | 1.00 | 5.00 |
| SDF-1 | 30.00 | 100.00 |
| Total | 191.00 | 1105.00 |

The chemotactic factors present in the combination of the invention are reported in Table 4:

TABLE 4

Chemotactic factors in PMF (pg/mg)

|  | Val min | Val max |
|---|---|---|
| EOTAXIN | 5.00 | 20.00 |
| MCP-1 | 1.00 | 4.00 |
| total | 6.00 | 24.00 |

The antibacterial/antiviral factors present in the combination of the invention are reported in Table 5

TABLE 5

Antibacterials/Antivirals in PMF (microgram/mg)

|  | Val min | Val max |
|---|---|---|
| Transferrin | 2.00 | 20.00 |
| Lactoferrin | 1.00 | 5.00 |
| Lysozyme | 5.00 | 20.00 |
| Lactoperoxydase | 10.00 | 30.00 |
| Total | 18.00 | 75.00 |

The complement C3a C4a proteins present in the combination of the invention are reported in Table 6.

TABLE 6

Complement proteins in PMF

|  | Val min | Val max |
|---|---|---|
| C3A | 0.20 | 0.70 |
| C4A | 0.90 | 2.00 |
| total | 1.10 | 2.70 |

The data reported in Tables 1-6 were obtained by commercially available sandwich ELISA methods specific for bovine molecules and flexible Bio-Plex® system (Bio-Rad Lab., Hercules, Calif., USA). The term "about" means a variation off 10%, preferably ±5% of the given value.

The main physiological roles of the components of the combination are reported below.

COMPLEMENT PROTEINS C3/C4: The complement consists of circulating proteins able to interact with the biological membranes and with specific receptors situated on the surface of various cell types, which induce inflammatory reactions that help combat infection.

Growth Factors

TGF-β1—TRANSFORMING GROWTH FACTOR: stimulates the production of Class A immunoglobulins, which are responsible for immune defences in the mucosa. Modulates cell proliferation and stimulates the deposit of extracellular matrix.

EGF—EPIDERMAL GROWTH FACTOR: regulates the development of the mucosa. Promotes the formation of epithelial cells.

IGF 1—INSULIN-LIKE GROWTH FACTOR: modulates cell proliferation, adhesion and migration and induces maturity of the mucosa.

VEGF—VASCULAR ENDOTHELIAL GROWTH FACTOR: stimulates blood vessel production. Presents mitogenic activity and activation of vascular permeability.

FGF-b—FIBROBLAST GROWTH FACTOR BASIC: stimulates proliferation of cells of mesenchymal origin such as fibroblasts, endothelial cells, astrocytes and keratinocytes. It also acts as a chemotactic factor.

GH—GROWTH HORMONE: general growth factor of all tissues.

GHRF—GROWTH HORMONE RELEASING FACTOR: stimulates the release of GH. required for normal postnatal growth, bone growth, regulatory effects on protein, carbohydrate, and lipid metabolism.

NGF—NERVE GROWTH FACTOR: stimulates activity and regulates growth and differentiation of the sympathetic system.

PDGF—PLATELET DERIVED GROWTH FACTOR: growth of differentiation of cells of mesodermal origin BMP-2—BONE MORPHOGENETIC PROTEIN 2: Development of bone and cartilage, cardiac cell differentiation.

Chemotactic Factors

EOTAXIN: binds to the chemokine receptors to recruit eosinophils to inflamed tissues.

MCP-1: Monocyte chemotactic factor-1: promotes aggregation of monocytes to inflamed tissues.

Cytokines

IL-1Ra inhibits the activities of interleukin 1 alpha and interleukin 1-beta, modulating a variety of IL 1 related immune and inflammatory responses.

IL-2 induces proliferation of T lymphocytes.

IL-4 possesses anti-inflammatory activity.

IL-6 stimulates innate and adaptive immunity.

IL-9 is a regulator of haemopoietic cells, stimulates cell proliferation and prevents apoptosis.

IL-17 regulates the activities of NF-KB and boosts nitric oxide (NO) production.

IL-10 has pleiotropic effects in immunoregulation and inflammation. Improves B cell survival, and therefore antibody production. Studies conducted on Knockout mice demonstrate that this protein is essential in immunoregulation of the mucosa. IL-12 stimulates T and natural killer cells.

IL-15 regulates T and natural killer cell activation and proliferation.

Interferon-gamma has known antiviral, antitumoral and immunoregulatory activities. It is a powerful macrophage activator and activates cell-mediated activity against bacteria and viruses.

TNF-α—Tumour necrosis factor stimulates the migration of neutrophils and monocytes to the site of infection.

Stem Cell Stimulating Factors

GM-CSF-granulocyte colony stimulating factor: is involved in the stimulation and peripheral dismission of immune progenitors from the bone marrow.

LIF—Leukemia inhibitory factor: pleiotropic cytokine with roles in several different systems, involved for instance in the induction of hematopoietic differentiation in normal and myeloid leukemia cells, induction of neuronal cell differentiation, regulator of mesenchymal to epithelial conversion during kidney development.

SCF-Stem cell factor: acts in utero in germ cell and neural cell development and hematopoiesis.

SDF-1-stromal derived factor-1: acts as a chemotactic factor of stem-progenitor cells expressing the CXCR4 ligand.

Antibacterials

Transferrin: delivers iron to red blood cells and prevents bacteria and viruses binding to iron.

Lactoferrin: deprives bacteria and viruses of iron required for their growth.

Lysozyme: has antibacterial effects in view of its enzymatic activity and as a consequence of its cationic and hydrophobic properties.

Lactoperoxydase: inhibits bacterial metabolism by oxidation of essential protein SH groups.

The combination of the invention may be prepared by extraction of colostrum, serum from pre-partum mammals or placenta according to the methods detailed below.

The serum has the highest peak of the factors in the last days before the birth, colostrum in the first hours after birth and no later than the 6th hour.

After 12 hours of delivery, the factors in colostrum decrease significantly and at 24 h many of them are no longer detectable.

These factors are genetically highly conserved in different species and therefore it is possible to use factors isolated from other mammalian species such as cattle, horses, camels, marine mammals, etc.

The factors are controlled with ELISA assays, specific for the species, even if the interspecies cross-reaction is very high because the factors are phylogenetically very conserved and are therefore qualitatively measurable also with ELISA used for different species (eg human-bovine and vice versa).

Extraction from Mammalian Serum

The serum of mammals pregnant females has the highest peak of the components of the combination of the invention in the last days before the delivery or parturition, usually in the last 5-15 days.

A typical procedure for the preparation of the combination of the invention is described.

1 liter of blood is drawn in 4 days for a total of 4 samples to prevent damage to the animal, preferably bovine or equine.

Serum is separated from blood at room temperature for 24 h and then centrifuged to squeeze the clot.

Serum is recovered (approximately 30/40% of the total volume) and phenoxyethanol 2.5% and diazolidinyl-urea 1% are added thereto as antiseptic agents. The serum so treated is then subjected to the following steps.

Ultrafiltration 300,000 Da:

The serum sample (frozen at −20° C.) obtained by coagulation and centrifugation from mammalian blood is thawed at room temperature and diluted with 2 volumes of demineralized water. The resulting solution is ultrafiltered through a Millipore BIOMAX® PELLICON® (ultrafiltration cassette with polyethersulfone and untracel regenerated cellulose membrane) 300,000 Da plane tangential flow membrane in polyethersulfone at Pi of 0.5 to 1 bar, in a cold room at 4° C.

The retentate and a fraction corresponding to about 1:10 of the permeate are transferred into a 1000 Da dialysis tube from Spectrum SPECTRAPOR® (dialysis membrane) in regenerated cellulose and dialyzed against demineralized water.

Ultrafiltration 5,000 Da:

The remaining permeate is ultrafiltered through a 5000 Da membrane. The permeate from the 300,000 Da ultrafiltration is concentrated on a 5000 Da plane tangential flow membrane Millipore BIOMAX® PELLICON® in polyethersulfone at Pi from 0.5 to 1 bar, cold room at 4° C.

The retentate is transferred to a 1,000 Da dialysis tube in regenerated cellulose from Spectrum SPECTRAPOR® and dialyzed against demineralized water (this dialysis also removes the preservatives). The product is then immediately lyophilized.

Extraction from Placenta

Bovine, equine or suine placenta is preferably used.

Homogenization

The placenta (frozen at −20° C.) is thawed at room temperature, cut into small pieces, washed with copious amounts of cold (4° C.) physiological saline (NaCl 0.9%) and homogenized using a Siramm cutter in a lysis buffer having the following composition: Tris/HCl 50 mM, EDTA 25 mM, TRITON® X-100 (octylphenol ethylene oxide condensate) 0.001% at pH 7.4. NaCl to a concentration of 0.9% is added to the suspension obtained. The suspension is stirred (magnetic stirrer) for 2 hours and maintained static overnight in a cold room at 4° C.

Centrifugation

The suspension was centrifuged at 13,000 rpm with a Sorvall RC6 and rotor SLA 15000 for 45 minutes at 4° C. The supernatant from the centrifugation is recovered, vacuum pre-filtered on DICALITE® (natural diatomite earth) and regenerated cellulose filters from 0.45 µm to 0.22 µm.

Ultrafiltration 300,000 Da

The product is filtered and ultrafiltered through a 300.000 Da Millipore BIOMAX® PELLICON® plane tangential flow membrane in at Pi of 0.5 to 1 bar, in a cold room at 4° C.

Ultrafiltration 5,000 Da

The permeate from the 300,000 Da ultrafiltration is concentrated on a 5000 Da Millipore BIOMAX® PELLICON® flat tangential flow membrane in polyethersulfone at Pi of 0.5 to 1 bar, in a cold room at 4° C. The retentate is transferred to a 1,000 Da dialysis tube from Spectrum SPECTRAPOR® in regenerated cellulose and dialyzed against demineralized water and then immediately lyophilized.

Extraction from Colostrum

Bovine colostrum is preferred, in particular from Holstein (Friesian) and Guernsey cows. It has been demonstrated that these cows produce the colostrum with the highest concentration of growth factors, immune modulators, chemotactic factors and antibacterial/antiviral factors. The cows are preferably calving for the second or third time. Colostrum is preferably collected not later than the 5$^{th}$-6th hour after calving, preferably colostrum collected one hour after calving, because the highest concentration of active substances is found during that period, while from the sixth hour onwards the active factors decline rapidly (only 20% are present 24 hours after calving).

The colostrum collected is tested for tuberculosis, cytotoxicity on cell cultures, mycoplasma, prions and human and bovine viruses.

The colostrum in the udder cistern is practically sterile, but once milked, despite all precautions, due to the high concentration of growth factors, its bacteria count rises very rapidly during freezing and thawing, which are rather slow processes in view of the high density of colostrum in the first few hours.

The concentration of preservatives allowed for dietary use and those allowed for parenteral and/or intravenous use is not sufficient to stop the bacteria count. The use of γ rays only produces sterile colostrum if radiation exceeding 10 Kgy is used, but this destroys a large part of the active factors, and in any event this method does not prevent the formation of pyrogens, the intravenous and/or topical use of which is prohibited in areas in contact with the blood and lymph nodes. An innovative collection system has therefore been devised to obtain a sterile, allergen-free compound, without preservatives or pyrogens.

Antiseptic agents in sufficient quantities to guarantee sterility and absence of pyrogens are added to the colostrum collected in sterile tanks (which are sterilised empty at 25 Kgy). Potassium sorbate and sodium benzoate are preferably used, each at the concentration of 12.5% (a much higher concentration than normally used, namely 0.2%), or alternatively, phenoxyethanol at the concentration of 2.5% or diazolidinyl urea at the concentration of 1%.

The colostrum thus treated does not need to be stored frozen before the active factor extraction processes, which leads to an obvious saving of costs.

The colostrum is then diluted with saline solution: this dilution not only gives better filtration without clogging the filter pores, but above all allows the release of active factors bonded to fats and casein. The colostrum thus diluted undergoes tangential microfiltration (ceramic membranes with a cut-off between 2 and 6 μm, temperature 5/20° C., transmembrane pressure between 0.2 and 2 bars), which may be repeated, to obtain an opalescent solution free of casein, fat matrix and milk proteins. All these substances constitute over 90% of the allergic content of colostrum and cow's milk. The solution is then passed through membranes, or alternatively a molecular sieve with a cut-off at 300,000 daltons (Da), for further purification of the active factors, all weighing less than 200,000 daltons.

The solution is then dialysed by ultrafiltration (cut-off 1000/2000 daltons) at high pressure, and then immediately freeze-dried. The result is a sterile, preservative-free, anallergic powder (casein and lactoalbumin are responsible for over 95% of allergies to cow's milk) of very high solubility, with the maximum possible concentration of active factors.

Depletion of Immunoglobulins

The immunoglobulins IgG, IgA and IgM are quantitatively depleted from the fractions obtained by the previously disclosed extractions by a method consisting of the following steps: 1) IgG depletion by affinity chromatography; 2) IgA and IgM depletion by tangential flow filtration and using membranes with a cut-off of 100 kDa; 3) desalting and concentration by dia-filtration using membranes with a cut-off of 3 kDa; 4) lyophilization.

IgG Depletion by Affinity Chromatography

The most popular techniques so far adopted for antibody purification are based on affinity chromatography using the highly specific immunoglobulin-binding proteins (IBP) isolated from the surface of bacteria, such as protein A from Staphylococcus aureus and protein G from Streptococci. Such proteins are usually immobilized in preparative chromatographic columns and capture immunoglobulins in a high degree of purity and recovery in only one step. The most suitable bovine IBP, characterized by the highest affinity towards IgG, from was selected and HITRAP columns (pre-packed ion-exchanged columns) containing 5 ml of protein A or G immobilized on SEPHAROSE® (cross-linked, beaded-from of agarose) were tested. By measuring IgG depletion by both electrophoresis and ELISA we found that protein G is the most suitable IBP for bovine IgG, reaching a depletion higher than 95%. The use of an HISCALE™50 column T-9 (presure-stable, empty column) is preferred, containing 400 ml of Protein G SEPHAROSE® 4 Fast Flow (GE Healthcare) consisting of recombinant protein G immobilized on SEPHAROSE® by cyanogen bromide (CNBr) which is able to bind 23 mg of IgG per ml for a total amount of almost 1 g. The mobile phase is eluted by a FPLC system (AKTAprime plus, GE Healthcare) and monitored by an UV detector at 280 nm, a conductivity meter (0.001-999.9 mS/cm), and a pHmeter. The affinity chromatography method consists of the following steps: 1) binding; 2) elution; 3) column regeneration. The binding step consists of equilibrating the column with 5 volumes of the binding buffer (phosphate buffer, 20 mM pH 7) at a flow-rate of 20 ml/min and not exceeding a back pressure of 0.1 MPa. The sample of extract is then loaded onto the column and then eluted with the binding buffer. During this stage, the immunoglobulins bind to the stationary phase while the other proteins are eluted from the column. Collection of the eluted proteins depleted from IgG is automatically driven by monitoring the UV of the eluate. The next step consists of eluting the immunoglobulin by using an acid mobile phase at pH 2.5 (Glycine-HCl) set at a flow rate of 20 ml/min. After the elution step it is necessary to flush ethanol (20%) into the column for its correct regeneration and storage.

IgA and IgM Depletion by Tangential Flow Filtration.

Separation of the IgM and IgA subclasses is based on their high molecular weight in respect to the proteome of the obtained fractions. In particular, bovine secretory IgA (SIgA) from bovine colostrum (mol. wt. about 410,000) is composed of four alpha-chains (mol. wt. 61,000), four light chains (mol. wt. 23,000) and one molecule of glycoprotein-a (mol. wt. 70,000-86,000). IgM forms polymers where multiple immunoglobulins are covalently linked together with disulfide bonds, mostly as a pentamer but also as a hexamer; so IgM is characterized by a molecular mass of at least 970 kDa (in its pentamer form). Depletion of these two classes of Ig is carried out by a tangential filtration system based on the use of porous membranes with a cutoff of 100 KDa. In particular the system is based on hollow fiber cross flow filtration cartridges which include a feed port, retentate port, and two permeate ports and a peristaltic pump, for gentle recirculation of biological fluids.

Desalting and concentration by diafiltration and 4) lyophilization. The proteome depleted of immunoglobulins is then dia-filtered through membranes with a 3-5 kDa cut-off for desalting and concentration. The resulting solution is then filtered through 0.2 micron membranes in sterile conditions and finally lyophilized.

Lyophilization:

The ultrafiltration retentate from 5000 Da is filtered under vacuum on Millipore filters made of cellulose regenerated from 0.2 μm, frozen at −20° C. and lyophilized.

The products obtained from serum, placenta or colostrum may be used separately or they may be pooled together. The products will in any case meet the quantitative ranges specified in Tables 1-6.

The combination of the invention is advantageously used, either parenterally or topically, in the treatment of conditions requiring tissue repair and regeneration, for the substitution of stem cell therapies. In particular, the combination of the invention, containing the same components of the supernatant of stem cell cultures, are useful for the treatment of bone traumatic and degenerative pathologies, as fillers for use in dermatology and plastic and aesthetic surgery, possibly in combination with a biomaterial such as collagen, hyaluronic acid, MATRIGEL® (a biological cell culture substrate), hydrocolloids, polylactides, polyglycolides, polycaprolactones etc. The amount of the combination of the invention to be administered can vary from 0.1 to 10 g. The combination of the invention may also be used to impregnate the scaffolds, brackets, implants or prostheses to give materials containing the combination of the invention in concentrations ranging from 1 to 10%, useful for the treatment of metastatic bone lesions, atrophy of the mandibular or maxillary alveolar process and for consolidation of bone fractures. The concentration will obviously depend on the extension and kind of lesion to be treated by the PMF containing material.

For the parenteral treatment, the combination of the invention will be formulated with suitable carriers and excipients in suitable dosage such as sterile solutions.

The combination may also be used as a restorative material for cavities for the therapy of pit caries and pulpar inflammation. For this purpose the combination will be formulated in form of scaffolds, cements, supports, re-absorbable or non-re-absorbable implants.

The daily dosage of the combination will depend on the kind and severity of the condition to be treated as well as on the patient's conditions, age and sex. It will generally range from 1 to 10 g daily, in one or more administrations, typically two to three administrations.

For the topical treatment, suitable administration forms include creams, ointments, gels, powders, lotions, mouthwashes, patches, comprising typically from 10 to 20% by weight of the combination of the invention. The combination of the invention obtained from colostrum, serum or placenta, if desired may be coated for specific applications, for instance in controlled releases forms, preferably into microspheres.

The formulations may contain other ingredients useful for specific uses.

The invention will be described in more detail in the following experimental part, given by way of examples.

Example 1

Treatment of Bone Diseases

In Vitro Tests
Ex Novo Osteogenesis

The effect of PMF on osteogenesis was evaluated in vitro by proliferation and differentiation assays of human and mouse osteogenic mesenchymal stem cells, progenitors of bone. In vivo, the of osteogenic activity of PMF was evaluated in a model of subcutaneous injection of MATRIGEL®, amorphous matrix, containing PMF and hydroxyapatite.

Proliferation

The effects of PMF on cell proliferation were evaluated using human osteoblasts (Saos-2 and MG-63) cells and human mesenchymal stem cells, as a model of osteoblast precursors (human Adipose tissue-derived Stem Cells, hASC).

The ASC were isolated (Zuk P A et al. Tissue Eng, 2001, 7: 211-28) from 6 volunteers donors and kept in control medium (DMEM supplemented with sodium pyruvate, 10% FCS, 100 U/ml penicillin, 100 mg/ml streptomycin and 250 ng/ml amphotericin B). Osteoblasts Saos-2 (ATCC number: HTB-85) and MG-63 (ATCC number: CRL-1427) were purchased from ATCC. Saos-2 and MG-63 were maintained respectively in McCoy'5A (Gibco, Life Technologies) with 15% FBS, and in DMEM with 10% FCS.

The cells were seeded in 96-well plates and subjected to MTT test on days 1, 3, 5 and 7 and were maintained in a 5% $CO_2$ humidified atmosphere at 37° C. PMF showed a potent dose-dependent proliferative effect on all the lines studied, maximum at the concentration of 5 mg/ml.

Migration

The ability of PMF to recruit mesenchymal progenitors (ASC) and human osteoblasts (MG-63 and SAOS) was evaluated by a wound healing assay, recognized as a key test for the study of the ability to induce cell motility. PMF at the indicated concentration (5 mg/ml) promotes cell motility in a manner comparable to the condition of positive control (10% FBS) for ASC and MG-63 and to a lesser extent, even though always statistically significant, for Saos.

Functionalization of Titanium Surfaces by Means of PMF

Cylinders in smooth titanium, commonly used to test in vitro the surfaces of dental implants, were coated with polyacrylate thin films to allow the functionalization of PMF. The introduction of carboxylic groups on the surface allows, in fact, the formation of covalent bonds with the amino groups present in the amino acid residues of growth factors contained in PMF. Saos-2 human osteoblasts were seeded on the samples, fixed after 3 and 6 hours and prepared for immunocytochemical analysis. After just 3 hours, it is possible to note a greater spreading of the cells on the treated surfaces compared to those not treated, while at 6 hours after seeding the spreading is similar in the two conditions, but the number of cells is significantly greater for functionalized surfaces.

In Vivo Tests
In Vivo Model of Osteogenesis in Matrigel.

The osteogenic activity of PMF was evaluated by inoculating subcutaneously MATRIGEL® into Balb-C in the presence or absence of 100 micrograms/ml of PMF. The examination of the PMF containing matrix showed a recruitment of inflammatory cells 10-15 days after inoculation.

Subsequent studies have been conducted in the presence of hydroxyapatite, added to the MATRIGEL® containing PMF or not. Ten days after inoculation, macrophages and reactive giant cells were recruited in the presence of PMF around hydroxyapatite crystals. Immunohistochemical analysis also showed the deposition of osteocalcin. At 60 days, calcification areas, surrounded by reactive stroma, positive for calcium deposition at Von Kossa staining, were evident.

From the above results, it is evident how PMF plays a role in enhancing osteogenesis, when it soluble osteoinductive factors are supplied in the culture medium or in hydroxyapatite scaffolds, in vivo. PMF can therefore conveniently be exploited in bone substitutes materials used in orthopedics and dentistry. Furthermore, PMF has capacities of positive chemotaxis on tested cells and can be used for the functionalization of implant surfaces. The effects on progenitor proliferation and migration of bone and osteoblasts are due to the presence in PMF of various chemokines and growth factors.

Bone Fractures in Dogs

Scaffolds containing from 3 to 15 g of PMF were placed between the bone fracture and the plaque in five dogs with fractures of long bones at high risk of nonunion or delayed union.

An increase in bone mass compared with untreated control dogs was observed. In particular, the formation of new bone trabeculae was observed thanks to the action of physiological osteoblasts stimulated by specific growth factors contained in the PMF. A more rapid consolidation of fractures and a mineralization of bone callus was observed in half the time normally required by the type of fracture taken into consideration. The average time of fracture consolidation decreased form 30 weeks for non treated animals to 16 weeks for PMF treated animals.

The results obtained show that PMF enables the activation of bone regeneration. Said results are very encouraging from the clinical and physiological point of view for the use in the presence of fractures at high risk of consolidation.

Example 2

Therapy of Penetrating Caries in Teeth and of Pulpar Inflammation

In Vivo Pulp Injury

Ten Sprague-Dawley rats, three months old, were used for the model of damage to the dental crown and subsequent filling according to the protocol of Garber S E et al., (J. Endod. 35 (2009), 60-64). On day zero holes were practiced on the right mesial surface of molars and fillings with calcium hydroxide or 200 micrograms of PMF have been applied in the cavities. Two teeth were left open as a positive control of pulpar inflammation.

Results

Figure 1A:
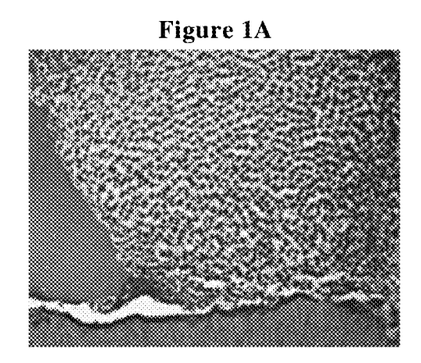
FIG. 1A is a positive control showing a marked inflammatory infiltrate.
Figure 1B:
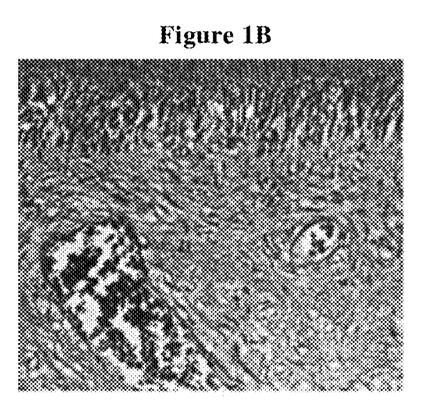
FIG. 1B shows teeth treated with calcium hydroxide having pulpitis with hyperemia and edema.
Figure 1C:
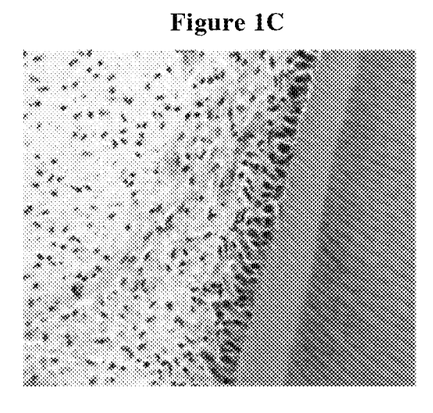
FIG. 1C shows the PMF containing fillings preserved the characteristics of a normal pulp.

Positive controls showed a marked inflammatory infiltrate (FIG. 1A), whereas the teeth treated with calcium hydroxide showed of pulpitis with hyperemia and edema (FIG. 1B). The PMF containing fillings preserved the characteristics of a normal pulp (FIG. 1C).

Example 3

Dermal Regeneration

In Vitro Tests

PMF considerably increased (>100%) the proliferative capacity of mesenchymal stem cells derived from human adipose tissue (hASCs) compared to control (10% FBS). PMF used at two different concentrations (5 mg/ml and 1 mg/ml), in the culture medium, had an effect dependent on the dose and on the time of incubation.

In Vivo Tests

PMF (100 γ) was mixed with 1 ml of non-crosslinked hyaluronic acid. The hyaluronic acid or other vehicles, such as MATRIGEL®, are designed to release PMF in a time of 15-20 days so as to allow a regeneration of dermis and collagen prolonged in time.

In Vivo Cell Proliferation

A mixture of PMF, MATRIGEL® or hyaluronic acid is injected subcutaneously in mice. After 7 days, vascular cell proliferation is observed and the periphery of the support amorphous. After 20 days the amorphous support is fully colonized by cells. After further 30 days a significant formation of collagen is observed.

Mechanical Injury to the Pig Tail: Intradermal Therapy

The ligature of the tail of pigs produces necrosis downstream of the tail. The experimental model involves the injection upstream of: 1) Physiological, 2) saline+PMF, 3) hyaluronic acid+PMF.

After injection of saline, upstream of the lesion, the tails fall in 24 hours. After 15 days from the injection, upstream of the lesion, of physiological+PMF, the tails do not fall, but begin to grow under less than optimal conditions; especially in the distal portions to the lesion necrotic lesions can be seen and no growth of the bristles occurs. After 15 days from the injection of hyaluronic acid+PMF upstream of the lesion, the tails are perfectly normal.

Histological examination shows that no alteration of nerves and muscles is observed in treated animals, the skin and vasculature of which return to physiological conditions. The tail sections of the untreated animals, besides having a diameter approximately half that of the treated animals, show extensive sclerosis, with total atrophy of the neuron-muscular, vascular and dermal components. The arteries are completely blocked by intimal plaques.

Example 4

Repair of Cardiac Muscle

The damage of the cardiac muscle by a syringe needle was prevented by releasing from the needle itself MATRIGEL®+100 micrograms of PMF. Colonisation of the lesion by muscle cells first occurs followed by complete repair.

The invention claimed is:

1. A pharmaceutical composition comprising a biomaterial and a combination of cytokines, growth factors, chemotactic factors, stem cell stimulating factors, antibacterial and/or antiviral factors and complement proteins, wherein the combination comprises all the components listed in the following tables:

cytokines

|  | Minimal Concentration (pg cytokine/mg combination) | Maximal Concentration (pg cytokine/mg combination) |
| --- | --- | --- |
| Interleukin-1a | 0.80 | 2.90 |
| Interleukin-1b | 0.02 | 0.09 |
| Interleukin-2 | 1.00 | 10.00 |
| Interleukin-4 | 0.04 | 0.17 |
| Interleukin-6 | 1.00 | 5.00 |
| Interleukin-8 | 0.10 | 0.70 |
| Interleukin-9 | 0.50 | 7.00 |
| Interleukin-10 | 0.50 | 2.80 |
| Interleukin-12 | 1.50 | 2.10 |
| Interleukin-15 | 1.00 | 10.00 |
| Interleukin-17 | 20.00 | 150.00 |
| Interferon-gamma | 5.00 | 50.00 |
| Tumor necrosis factor α | 30.00 | 70.00 |
| Interleukin-1 Receptor Agonist | 10.00 | 30.00 |
| Sum | 71.46 | 340.76 | and growth factors:

|  | Minimal Concentration (pg growth factor/mg combination) | Maximal Concentration (pg growth factor/mg combination) |
|---|---|---|
| Transforming growth_factor-β1 | 100.00 | 500.00 |
| Insulin-like growth factor-1 | 1000.00 | 5000.00 |
| Nerve growth factor | 2.00 | 5.00 |
| Platelet-derived growth factor | 10.00 | 50.00 |
| Epidermal growth factor | 4.80 | 9.40 |
| Bone morphogenetic protein | 15.00 | 50.00 |
| Fibroblast growth factor basic | 100.00 | 500.00 |
| Fibroblast growth factor-2 | 5.00 | 20.00 |
| Hepatocyte growth factor | 50.00 | 100.00 |
| Vascular endothelial growth factor | 35.00 | 260.00 |
| Sum | 1321.80 | 6494.40 | and stem cell stimulating factors:

|  | Minimal Concentration (pg stem cell stimulating factor/mg combination) | Maximal Concentration (pg stem cell stimulating factor/mg combination) |
|---|---|---|
| Granulocyte colony-stimulating factor | 10.00 | 50.00 |
| Granulocyte-macrophage colony-stimulating factor | 100.00 | 750.00 |
| Leukemia inhibitory factor | 50.00 | 200.00 |
| Stem cell factor | 1.00 | 5.00 |
| Stromal derived factor-1 | 30.00 | 100.00 |
| Sum | 191.00 | 1105.00 | and chemotactic factors:

|  | Minimal Concentration (pg chemotactic factor/mg combination) | Maximal Concentration (pg chemotactic factor/mg combination) |
|---|---|---|
| EOTAXIN-1, EOTAXIN-2, and/or EOTAXIN-3 | 5.00 | 20.00 |
| Monocyte chemotactic factor-1 | 1.00 | 4.00 |
| Sum | 6.00 | 24.00 | and antibacterial and/or antiviral factors:

|  | Minimal Concentration (μg antibacterial and/or antiviral factors/mg combination) | Maximal Concentration (μg antibacterial and/or antiviral factors/mg combination) |
|---|---|---|
| Transferrin | 2.00 | 20.00 |
| Lactoferrin | 1.00 | 5.00 |
| Lysozyme | 5.00 | 20.00 |
| Lactoperoxydase | 10.00 | 30.00 |
| Sum of the above antibacterial and/or antiviral factors | 18.00 | 75.00 | and complement proteins:

|  | Minimal Concentration (pg complement protein/mg combination) | Maximal Concentration (pg complement protein/mg combination) |
|---|---|---|
| Complement C3A | 0.20 | 0.70 |
| Complement C4A | 0.90 | 2.00 |
| Sum | 1.10 | 2.70 | wherein the biomaterial is selected from the group consisting of: collagen, hyaluronic acid, a gelatinous protein mixture secreted by Engelbreth-Holm-Swarm mouse sarcoma cells, hydrocolloids, polylactides, polyglycolides, and polycaprolactones.

2. The composition according to claim 1, wherein the combination is obtained by extraction of colostrum.

3. The composition according to claim 1, wherein the combination is obtained by extraction of placenta.

4. The composition according to claim 1, wherein the combination is obtained by extraction of serum collected 5-15 days before partus.

5. The composition according to claim 1, for use as fillers in dermatology, plastic surgery, or aesthetic surgery.

6. A pharmaceutical composition comprising the composition of claim 1 as the active ingredient in admixture with suitable carriers and/or excipients.

7. The pharmaceutical composition according to claim 6, for parenteral administration.

8. The pharmaceutical composition according to claim 6, for topical administration.

9. An implantable material in a form of scaffolds, cements, supports, re-absorbable implants, or non-reabsorbable implants, comprising a combination of cytokines, growth factors, chemotactic factors, stem cell stimulating factors, antibacterial and/or antiviral factors and complement proteins, wherein the combination comprises all the components listed in the following tables:

cytokines

|  | Minimal Concentration (pg cytokine/mg combination) | Maximal Concentration (pg cytokine/mg combination) |
|---|---|---|
| Interleukin-1a | 0.80 | 2.90 |
| Interleukin-1b | 0.02 | 0.09 |
| Interleukin-2 | 1.00 | 10.00 |
| Interleukin-4 | 0.04 | 0.17 |
| Interleukin-6 | 1.00 | 5.00 |
| Interleukin-8 | 0.10 | 0.70 |
| Interleukin-9 | 0.50 | 7.00 |
| Interleukin-10 | 0.50 | 2.80 |
| Interleukin-12 | 1.50 | 2.10 |
| Interleukin-15 | 1.00 | 10.00 |
| Interleukin-17 | 20.00 | 150.00 |
| Interferon-gamma | 5.00 | 50.00 |
| Tumor necrosis factor α | 30.00 | 70.00 |
| Interleukin-1 Receptor Agonist | 10.00 | 30.00 |
| Sum | 71.46 | 340.76 | and growth factors:

|  | Minimal Concentration (pg growth factor/mg combination) | Maximal Concentration (pg growth factor/mg combination) |
| --- | --- | --- |
| Transforming growth factor-β1 | 100.00 | 500.00 |
| Insulin-like growth factor-1 | 1000.00 | 5000.00 |
| Nerve growth factor | 2.00 | 5.00 |
| Platelet-derived growth factor | 10.00 | 50.00 |
| Epidermal growth factor | 4.80 | 9.40 |
| Bone morphogenetic protein | 15.00 | 50.00 |
| Fibroblast growth factor basic | 100.00 | 500.00 |
| Fibroblast growth factor-2 | 5.00 | 20.00 |
| Hepatocyte growth factor | 50.00 | 100.00 |
| Vascular endothelial growth factor | 35.00 | 260.00 |
| Sum | 1321.80 | 6494.40 | and stem cell stimulating factors:

|  | Minimal Concentration (pg stem cell stimulating factor/mg combination) | Maximal Concentration (pg stem cell stimulating factor/mg combination) |
| --- | --- | --- |
| Granulocyte colony-stimulating factor | 10.00 | 50.00 |
| Granulocyte-macrophage colony-stimulating factor | 100.00 | 750.00 |
| Leukemia inhibitory factor | 50.00 | 200.00 |
| Stem cell factor | 1.00 | 5.00 |
| Stromal derived factor-1 | 30.00 | 100.00 |
| Sum | 191.00 | 1105.00 | and chemotactic factors:

|  | Minimal Concentration (pg chemotactic factor/mg combination) | Maximal Concentration (pg chemotactic factor/mg combination) |
| --- | --- | --- |
| EOTAXIN-1, EOTAXIN-2, and/or EOTAXIN-3 | 5.00 | 20.00 |
| Monocyte chemotactic factor-1 | 1.00 | 4.00 |
| Sum | 6.00 | 24.00 | and antibacterial and/or antiviral factors:

|  | Minimal Concentration (μg antibacterial and/or antiviral factors/mg combination) | Maximal Concentration (μg antibacterial and/or antiviral factors/mg combination) |
| --- | --- | --- |
| Transferrin | 2.00 | 20.00 |
| Lactoferrin | 1.00 | 5.00 |
| Lysozyme | 5.00 | 20.00 |
| Lactoperoxydase | 10.00 | 30.00 |
| Sum of the above antibacterial and/or antiviral factors | 18.00 | 75.00 | and complement proteins:

|  | Minimal Concentration (pg complement protein/mg combination) | Maximal Concentration (pg complement protein/mg combination) |
| --- | --- | --- |
| Complement C3A | 0.20 | 0.70 |
| Complement C4A | 0.90 | 2.00 |
| Sum | 1.10 | 2.70 |

10. A pharmaceutical composition in a topical form of creams, ointments, gels, lotions, or patches, wherein the composition is a combination of cytokines, growth factors, chemotactic factors, stem cell stimulating factors, antibacterial and/or antiviral factors and complement proteins, which comprises all the components listed in the following tables:

cytokines

|  | Minimal Concentration (pg cytokine/mg combination) | Maximal Concentration (pg cytokine/mg combination) |
| --- | --- | --- |
| Interleukin-1a | 0.80 | 2.90 |
| Interleukin-1b | 0.02 | 0.09 |
| Interleukin-2 | 1.00 | 10.00 |
| Interleukin-4 | 0.04 | 0.17 |
| Interleukin-6 | 1.00 | 5.00 |
| Interleukin-8 | 0.10 | 0.70 |
| Interleukin-9 | 0.50 | 7.00 |
| Interleukin-10 | 0.50 | 2.80 |
| Interleukin-12 | 1.50 | 2.10 |
| Interleukin-15 | 1.00 | 10.00 |
| Interleukin-17 | 20.00 | 150.00 |
| Interferon-gamma | 5.00 | 50.00 |
| Tumor necrosis factor α | 30.00 | 70.00 |
| Interleukin-1 Receptor Agonist | 10.00 | 30.00 |
| Sum | 71.46 | 340.76 | and growth factors:

|  | Minimal Concentration (pg growth factor/mg combination) | Maximal Concentration (pg growth factor/mg combination) |
| --- | --- | --- |
| Transforming growth_factor-β1 | 100.00 | 500.00 |
| Insulin-like growth factor-1 | 1000.00 | 5000.00 |
| Nerve growth factor | 2.00 | 5.00 |
| Platelet-derived growth factor | 10.00 | 50.00 |
| Epidermal growth factor | 4.80 | 9.40 |
| Bone morphogenetic protein | 15.00 | 50.00 |
| Fibroblast growth factor basic | 100.00 | 500.00 |
| Fibroblast growth factor-2 | 5.00 | 20.00 |
| Hepatocyte growth factor | 50.00 | 100.00 |
| Vascular endothelial growth factor | 35.00 | 260.00 |
| Sum | 1321.80 | 6494.40 | and stem cell stimulating factors:

|  | Minimal Concentration (pg stem cell stimulating factor/mg combination) | Maximal Concentration (pg stem cell stimulating facto/mgr combination) |
|---|---|---|
| Granulocyte colony-stimulating factor | 10.00 | 50.00 |
| Granulocyte-macrophage colony-stimulating factor | 100.00 | 750.00 |
| Leukemia inhibitory factor | 50.00 | 200.00 |
| Stem cell factor | 1.00 | 5.00 |
| Stromal derived factor-1 | 30.00 | 100.00 |
| Sum | 191.00 | 1105.00 | and chemotactic factors:

|  | Minimal Concentration (pg chemotactic factor/mg combination) | Maximal Concentration (pg chemotactic factor/mg combination) |
|---|---|---|
| EOTAXIN-1, EOTAXIN-2, and/or EOTAXIN-3 | 5.00 | 20.00 |
| Monocyte chemotactic factor-1 | 1.00 | 4.00 |
| Sum | 6.00 | 24.00 | and antibacterial and/or antiviral factors:

|  | Minimal Concentration (µg antibacterial and/or antiviral factors/mg combination) | Maximal Concentration (µg antibacterial and/or antiviral factors/mg combination) |
|---|---|---|
| Transferrin | 2.00 | 20.00 |
| Lactoferrin | 1.00 | 5.00 |
| Lysozyme | 5.00 | 20.00 |
| Lactoperoxydase | 10.00 | 30.00 |
| Sum of the above antibacterial and/or antiviral factors | 18.00 | 75.00 | and complement proteins:

|  | Minimal Concentration (pg complement protein/mg combination) | Maximal Concentration (pg complement protein/mg combination) |
|---|---|---|
| Complement C3A | 0.20 | 0.70 |
| Complement C4A | 0.90 | 2.00 |
| Sum | 1.10 | 2.70. |

11. A pharmaceutical composition in a controlled release form, comprising a combination of cytokines, growth factors, chemotactic factors, stem cell stimulating factors, antibacterial and/or antiviral factors and complement proteins, wherein the combination comprises all the components listed in the following tables:

cytokines

|  | Minimal Concentration (pg cytokine/mg combination) | Maximal Concentration (pg cytokine/mg combination) |
|---|---|---|
| Interleukin-1a | 0.80 | 2.90 |
| Interleukin-1b | 0.02 | 0.09 |
| Interleukin-2 | 1.00 | 10.00 |
| Interleukin-4 | 0.04 | 0.17 |
| Interleukin-6 | 1.00 | 5.00 |
| Interleukin-8 | 0.10 | 0.70 |
| Interleukin-9 | 0.50 | 7.00 |
| Interleukin-10 | 0.50 | 2.80 |
| Interleukin-12 | 1.50 | 2.10 |
| Interleukin-15 | 1.00 | 10.00 |
| Interleukin-17 | 20.00 | 150.00 |
| Interferon-gamma | 5.00 | 50.00 |
| Tumor necrosis factor α | 30.00 | 70.00 |
| Interleukin-1 Receptor Agonist | 10.00 | 30.00 |
| Sum | 71.46 | 340.76 | and growth factors:

|  | Minimal Concentration (pg growth factor/mg combination) | Maximal Concentration (pg growth factor/mg combination) |
|---|---|---|
| Transforming growth factor-β1 | 100.00 | 500.00 |
| Insulin-like growth factor-1 | 1000.00 | 5000.00 |
| Nerve growth factor | 2.00 | 5.00 |
| Platelet-derived growth factor | 10.00 | 50.00 |
| Epidermal growth factor | 4.80 | 9.40 |
| Bone morphogenetic protein | 15.00 | 50.00 |
| Fibroblast growth factor basic | 100.00 | 500.00 |
| Fibroblast growth factor-2 | 5.00 | 20.00 |
| Hepatocyte growth factor | 50.00 | 100.00 |
| Vascular endothelial growth factor | 35.00 | 260.00 |
| Sum | 1321.80 | 6494.40 | and stem cell stimulating factors:

|  | Minimal Concentration (pg stem cell stimulating factor/mg combination) | Maximal Concentration (pg stem cell stimulating factor/mg combination) |
|---|---|---|
| Granulocyte colony-stimulating factor | 10.00 | 50.00 |
| Granulocyte-macrophage colony-stimulating factor | 100.00 | 750.00 |
| Leukemia inhibitory factor | 50.00 | 200.00 |
| Stem cell factor | 1.00 | 5.00 |
| Stromal derived factor-1 | 30.00 | 100.00 |
| Sum | 191.00 | 1105.00 | and chemotactic factors:

|  | Minimal Concentration (pg chemotactic factor/mg combination) | Maximal Concentration (pg chemotactic factor/mg combination) |
|---|---|---|
| EOTAXIN-1, EOTAXIN-2, and/or EOTAXIN-3 | 5.00 | 20.00 |
| Monocyte chemotactic factor-1 | 1.00 | 4.00 |
| Sum | 6.00 | 24.00 | and antibacterial and/or antiviral factors:

|  | Minimal Concentration (μg antibacterial and/or antiviral factors/mg combination) | Maximal Concentration (μg antibacterial and/or antiviral factors/mg combination) |
|---|---|---|
| Transferrin | 2.00 | 20.00 |
| Lactoferrin | 1.00 | 5.00 |
| Lysozyme | 5.00 | 20.00 |
| Lactoperoxydase | 10.00 | 30.00 |
| Sum of the above antibacterial and/or antiviral factors | 18.00 | 75.00 | and complement proteins:

|  | Minimal Concentration (pg complement protein/mg combination) | Maximal Concentration (pg complement protein/mg combination) |
|---|---|---|
| Complement C3A | 0.20 | 0.70 |
| Complement C4A | 0.90 | 2.00 |
| Sum | 1.10 | 2.70. |

12. A method for treating conditions requiring tissue repair and regeneration, comprising administering to a subject in need thereof the composition of claim 1, wherein the conditions are selected from the group consisting of: bone traumatic and degenerative pathologies, metastatic bone lesions, atrophy of the mandibular or maxillary alveolar process, bone fractures, pit caries, pulpar inflammation, cardiac muscle damages, and dermal damages.

\* \* \* \* \*